United States Patent [19]
Schmitt

[11] Patent Number: 6,065,705
[45] Date of Patent: May 23, 2000

[54] WEIGHT COMPENSATING APPARATUS, PARTICULARLY FOR A MEDICAL DEVICE

[75] Inventor: Thomas Schmitt, Forchheim, Germany

[73] Assignee: Siemens Aktiengesellschaft, Munich, Germany

[21] Appl. No.: 09/177,361

[22] Filed: Oct. 23, 1998

[30] Foreign Application Priority Data

Oct. 27, 1997 [DE] Germany .............. 197 47 393

[51] Int. Cl.[7] .................................. B65H 75/48
[52] U.S. Cl. .................. 242/375.1; 242/375.3; 242/382
[58] Field of Search .............. 242/375.1, 375.3, 242/375, 382

[56] References Cited

U.S. PATENT DOCUMENTS

| | | | |
|---|---|---|---|
| 1,004,753 | 10/1911 | Doust | 242/375.3 |
| 1,685,585 | 9/1928 | Grimes | 242/375.1 |
| 1,975,633 | 10/1934 | Cakora | 242/375.1 |
| 3,105,652 | 10/1963 | Becker et al. | 242/375.3 X |
| 3,384,321 | 5/1968 | Becker et al. | 242/375.1 |
| 4,531,688 | 7/1985 | Gall | 242/375 X |

FOREIGN PATENT DOCUMENTS

| | | |
|---|---|---|
| 1 481 875 | 5/1972 | Germany . |
| 87 06 358 | 10/1988 | Germany . |

*Primary Examiner*—Donald P. Walsh
*Assistant Examiner*—Emmanuel M. Marcelo
*Attorney, Agent, or Firm*—Hill & Simpson

[57] ABSTRACT

In a weight compensating apparatus, particularly for a medical device, a cable drum accepts a supporting cable which carries a load, this drum being biased by the force of a spiral spring element. A safety arrangement triggers a stopping arrangement given a breakage of the spiral spring element. The safety arrangement responds particularly to a breakage of the outer region of the spiral spring element.

3 Claims, 12 Drawing Sheets

WEIGHT COMPENSATING APPARATUS, PARTICULARLY FOR A MEDICAL DEVICE

BACKGROUND OF THE INVENTION

1. Field of the Invention

The present invention is directed to an apparatus for compensating for the weight of a supported object, such as for compensating for the weight of an x-ray radiator in a sealing-mounted medical device.

2. Description of the Prior Art

German Utility Model GM 87 06 358 teaches a weight compensating apparatus, particularly for a medical device, wherein a cable drum is provided for accepting at least one cable capable of carrying a weight such as an x-ray radiator, the cable drum being loadable by the force of a spiral spring element, and wherein a safety arrangement is provided for triggering a signal given a cable breakage. An electromagnetically actuatable friction brake is provided at the weight compensating apparatus which acts on the cable drum, or its cover, in order to be able to stop rotation thereof when the x-radiator, which is height-adjustable at a ceiling stand, is to be held in place in arbitrary vertical positions.

In this weight compensating apparatus a spring breakage could allow an unintentional displacement of the weight, i.e. the x-radiator, due to gravity as a result of the reduced counterforce caused by the breakage.

A break in the outer region of the spiral spring is particularly problematic, because this results in this outer region of the spiral spring braces itself at the spring drum, the counterforce essentially applied by the spiral spring then depending solely on the friction at the housing. As a result of such a spring breakage, the weight is slowly displaced according to the force of gravity. Safety means which act in the manner of a safety belt given a breakage of the inner region of the spiral spring could not respond to a breakage of the outer region of the spiral spring due to the abrupt cancellation of the counterforce emanating from the spiral spring.

SUMMARY OF THE INVENTION

It is an object of the present invention to construct a weight compensating arrangement of the abovementioned type wherein a spring breakage does not lead to the unintentional displacement of the load.

The above object is achieved in accordance with the principles of the present invention in a weight compensating apparatus, particularly for a medical device, wherein a cable which supports a load, such as an x-ray radiator, is wound around a cable drum, the cable drum being biased by a spiral spring element, and having a safety arrangement for triggering an arrangement for arresting rotation of the cable drum upon the occurrence of a breakage of the spiral spring element, the safety arrangement responding particularly to a breakage occurring at an outer region of the spiral spring element. To this end, an outer end of the spiral spring element engages a catch of the arresting arrangement so as to prevent displacement of the cable drum, the catch being biased by a catch spring, with the force of the catch spring being dimensioned such that, when the spiral spring element is loaded, the catch precludes arresting of the cable drum by the arresting arrangement only up to at least 50% of the weight of the load.

An advantage of the inventive apparatus is that a safety arrangement is provided for triggering a stopping mechanism given breakage of the spiral spring element, and particularly following a breakage of the outer region of the spiral spring element. Due to the releasing of the stopping arrangement, the displacement of the cable drum is advantageously prevented, so that the load is not unintentionally displaced due to gravity, which is particularly advantageous when the load is an x-ray radiator beneath which an examination subject may be disposed.

As stated above, the outer end of the spiral spring element engages a catch of the stopping arrangement for blocking the displaceability of the cable drum, this catch being loadable with a catch spring, and the force of the catch spring is proportioned such that in the loading or bending of the spiral spring element the catch spring cancels the arresting of the cable drum only when 50% of the load is attained. This results in the cable drum being released to allow its displacement only when a counterforce emanating from the spiral spring element of at least 50% of the load is attained or exceeded, and conversely, given a failure to exceed this counterforce, the catch of the stopping arrangement prevents displacement of the cable drum. The catch of the stopping arrangement consequently responds with certainty particularly given a breakage of the outer region of the spiral spring element, so that an undesirable displacement of the load, and the danger arising therefrom, are avoided. In this context it is particularly advantageous if in the loading of the spiral spring element for the catch to cancel the arresting of the cable drum only when at least 90% of the useful load is attained. The stopping arrangement is thus designed to be particularly sensitive to the abatement of the counterforce emanating from the spiral spring element. It is particularly advantageous for the force of the catch spring to be adjustable, so that the sensitivity of the response of the stopping arrangement is adjustable.

In a further embodiment of the weight compensating apparatus the safety arrangement includes a frangible cable extending at least along the outer perimeter of the spiral spring element, one end of this cable being connected to an inner region of the spiral spring element and the other end engaging at a spring-loaded catch for blocking the displaceability of the cable drum such that the catch is held in opposition to the force of a catch spring for releasing the cable drum. Given a breakage of the spring element this cable likewise breaks and the spring-loaded catch blocks rotation of the cable drum. In the framework of this embodiment it is advantageous to provide a number of such frangible cables, so that the individual cables can be constructed thin and thus a smaller space is required, or instead of a cable a ribbon, or a number of such ribbons, can be employed for this purpose.

In a further embodiment of the weight compensating apparatus the safety arrangement includes means for detecting the electrical resistance of a resistance element in connection with the spiral spring element as well as an electromechanically controllable stopping means for stopping the cable drum. A change in resistance of the resistance element which occurs given a breakage of the spiral spring element effects an actuation of the stopping means for stopping the cable drum. An electrical monitoring of a cable breakage is thus possible. It is particularly advantageous to employ the spiral spring element itself as the resistance element with at least one strain measuring element, and/or a wire—preferably a resistance wire—extending at least along an outer region of the spiral spring element.

In another version of the weight compensating apparatus a spring breakage can be detected wherein the safety means has at least one transponder arranged at the spiral spring element and one receiver for signals emanating from the transponder, with an actuation of the electromechanical stopping means being effected via the signals emanating from the transponder given a spring breakage. Such transponders require little space and are insensitive to rough handling. A number of transponders can be advantageously arranged along the spiral spring element, so that a breakage of the spiral spring element can also be determined at various points.

Another alternative is to arrange the spiral spring element with a recess for a tab in connection with the spiral spring element being arranged in the housing, and the tab being in connection with a locking mechanism such that the locking mechanism for stopping the cable drum is released when the tab reaches a mechanical limit of a prescribed adjusting path of the tab in the recess, whereupon a spring breakage is detected and a failure can be avoided. Such an arrangement is implemented in purely mechanical fashion and thus independent of any voltage supply. A number of such recesses for a number of such tabs in connection with the spiral spring element are provided in a preferred version, these tabs acting on the locking mechanism such that a spring breakage can also be detected at various points.

In another embodiment of the weight compensating apparatus the spiral spring element is arranged in a housing to which a vibration detector of a safety means is attached. Given a jarring of the housing caused by a breakage of the spiral spring element, the vibration detector generates a signal for the actuation of an electromechanical stopping means for blocking the displaceability of the cable drum. Such an embodiment can also be retrofitted to an existing weight compensating apparatus without great outlay.

A breakage of the spiral spring element can also be detected in an embodiment wherein, at least in the terminal region of the spiral spring element, the weight compensating apparatus has an axle mounted at the housing accepting the spiral spring element rotatably about said housing's longitudinal axis and perpendicularly to the longitudinal axis—at least one end thereof projecting over the housing. Given a displacement of the axle around its longitudinal axis due to spring breakage, a safety means coupled at the end of the axle effects stopping of the cable drum.

DESCRIPTION OF THE PREFERRED EMBODIMENT

Figure 1:
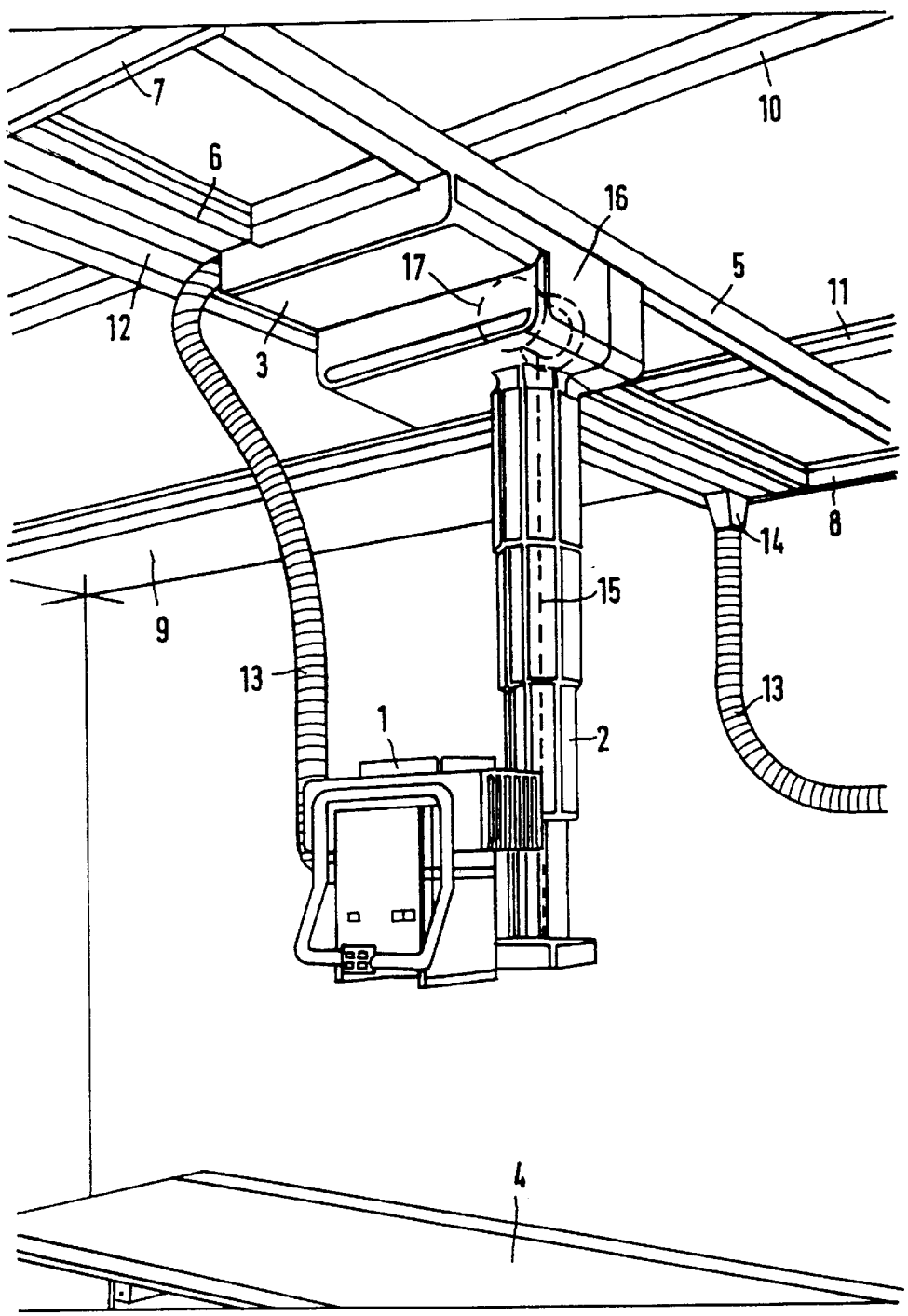
FIG. 1 is a perspective view of an x-ray examination device provided with an inventive weight compensating apparatus.
Figure 2:
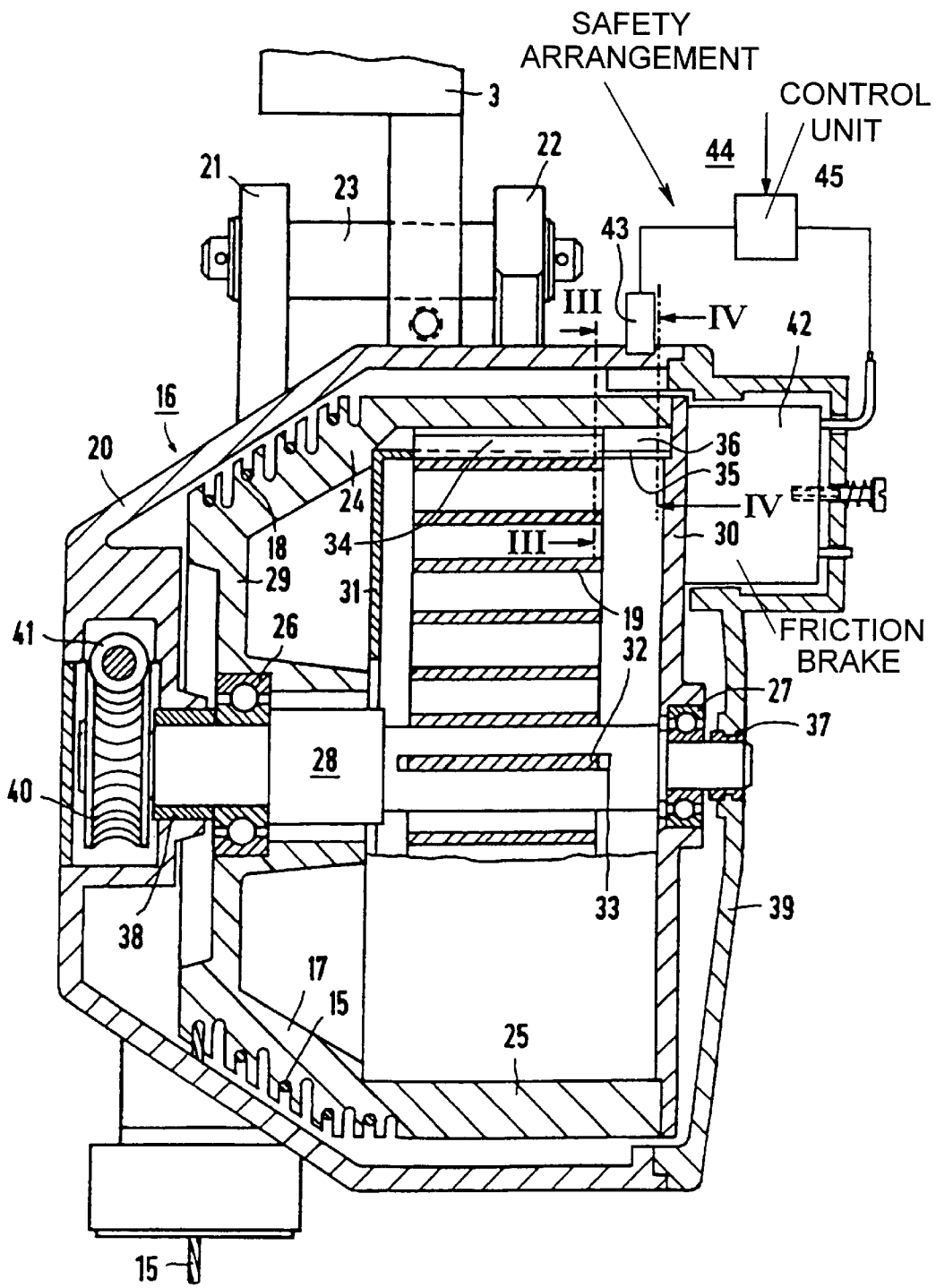
FIG. 2 is a longitudinal section through an inventive weight compensating apparatus.

FIG. 1 depicts a ceiling stand for an x-ray radiator 1 which is attached at a carriage 3 above an examination table 4 so as to be height-adjustable by means of a telescoping column 2. The carriage 3 can be displaced perpendicularly to the examination table 4 within parallel rails 5, 6 by means of rollers (not visible). The rails 5 and 6, connected by end pieces 7 and 8, are driveable by means of rollers (also not visible) along parallel ceiling rails 10 and 11 attached to the ceiling 9 of the examination room and running at a right angle to the rails 5 and 6, so that the x-radiator 1 is also displaceable along the examination table 4. A channel 12 in which a flexible cable 13 runs extends parallel to the rail 6, this cable entering the channel 12 through a lead-through 14 which is provided in the region of the end piece 8 and is stationary with respect to the carriage 3, and exiting the channel 12 in the region of the carriage 3, and being led to the x-ray radiator 1. As depicted in dashed fashion in FIG. 1, the x-radiator 1 is held by a supporting or carrying cable 15 which runs in the interior of the telescopic column 2 and which is secured at its lowest telescopic part. The supporting cable 15 leads to a weight compensating apparatus 16 (also shown dashed) which includes among other parts a cable drum 17 on which the supporting cable 15 can be rolled and unrolled (FIG. 2). To this end the supporting cable 15 runs in a spiral groove 18 provided in the shell of the cable drum 17, the winding radius of which varies over its length such that the weight of the x-ray radiator 1 attached to the supporting cable 15 is always compensated by the force of a spring 19 engaging the cable drum 17. The supporting cable 15 is secured at one end to the cable drum 17 (not depicted).

Extremely small forces suffice to adjust the height of the x-ray radiator 1, since the friction loss and the inertia of the mass to be moved need merely be overcome.

As FIG. 2 also depicts, the weight compensating apparatus has a housing 20 at which two brackets 21 and 22 are provided between which a bolt 23 extends by means of which the weight compensating apparatus 16 is attached to the carriage 3. The cable drum 17 is fashioned as a hollow body and is located in the interior of the housing 20. The cable drum 17 has a conical portion 24 provided with the spiral groove 18 and a cylindrical portion 25 at the larger end of the conical portion 24. The cable drum 17 is rotatably mounted at a shaft 28 by means of two ball bearings 26 and 27. The ball bearing 26 is accepted in the bore of a flange 29 which is provided at the smaller end of the conical portion 24 and which proceeds essentially radially, while the ball bearing 27 is accepted in a bore of a shield 30 which closes the cylindrical portion 25 at its free end.

The spring 19 is fashioned as a spiral spring and is accepted in a spring housing 31 which is in turn accepted in the bore of the cylindrical portion 25. One end 32 of the spring 19 is connected to the shaft 28 in torsionally secure fashion, such as by engaging in a slot 33. The other end 34 of the spring 19 is bent radially outwardly and projects from the spring housing 31 through a slot 35 therein (FIG. 3) in order to engage in a slot provided at the inner wall of the hollow-cylindrical opening 46 of a catch 36 mounted at the cylindrical portion 25 so that it is connected to the cable drum 17 in torsionally secure fashion. A torque acting on the cable drum 17 on the shaft 28—as arises given rolling and unrolling of the supporting cable 15, for example—is thus necessarily produced by a change of the force exerted on the cable drum 17 by the spring 19.

The shaft 28 is rotatably held in the housing 20 by means of two bearing bushings 37 and 38, the bearing bushing 38 being accepted in a bore of the housing 20 itself, and the bearing bushing 37 being accepted in a bore of a cover 39 that closes the housing 20. A worm gear 40 is attached in torsionally secure fashion at one end of the shaft 28, this worm gear meshing 40 with a worm 41 rotatably mounted in the housing 20 (not depicted). This worm-and-gear arrangement forms a self-contained train, so that a rotation of the shaft 28 in the bearing bushings 37 and 38 is only possible if the worm 41 is rotated (driven).

In the operational state depicted in FIG. 2 the x-ray radiator 1 is located in its uppermost position. The supporting cable 15 is accordingly completely rolled up in the spiral groove 18 provided on the shell of the conical portion 24 of the cable drum 17. Due to the torque produced by the worm 41 meshing with the worm gear 40, the spring 19 is biased so that the force exerted on the cable drum 17 by the spring 19 compensates the weight of the x-ray radiator 1; i.e., the torque exerted by the spring 19 by means of its end 34 engaging in the slot 46 is in balance with the torque exerted on the cable drum 17 by the weight of the x-ray radiator 1 via the supporting cable 15.

The path of the spiral groove 18 on the shell of the conical portion 24 of the cable drum 17 is selected in consideration of the spring characteristic of the spring 19 such that the torque exerted on the cable drum 17 by the spring 19 is in balance with the torque exerted on the cable drum 17 by the weight of the x-ray radiator 1 via the supporting cable 15, even if the supporting cable 15 is partially or completely unrolled from the cable drum 17.

In order to be able to hold the x-ray radiator 1 in arbitrary vertical positions, an electromagnetically actuatable friction brake 42 is provided which is accepted in the ceiling 39 and which acts on the cable drum 17, or its cover 30.

A first exemplary embodiment of an inventive weight compensating apparatus is also shown in FIG. 2. This includes a vibration detector 43 of a safety arrangement 44 disposed in the region of the spring housing 31—housing 20 in the exemplary embodiment. A control unit 45 for the friction brake 42 is connected to the vibration detector 43, for example, so that given the occurrence of a vibration caused by a breakage of the spring 19, a signal is generated by the vibration detector 43 which is fed to the friction brake 42 via the control unit 45 so that the brake 42 stops the cable drum 17. This embodiment of the invention is particularly advantageous if, for to greater safety, weight compensation apparatuses are to be retrofitted for the avoidance of damage given a spring breakage. If the spring 19 breaks in the outer region in particular, it strikes the spring housing 31, resulting in a vibration, which is detected by the vibration detector 43. This arrangement thus is suitable for detecting a spring breakage in the outer region of the spring 19.

Figure 3:
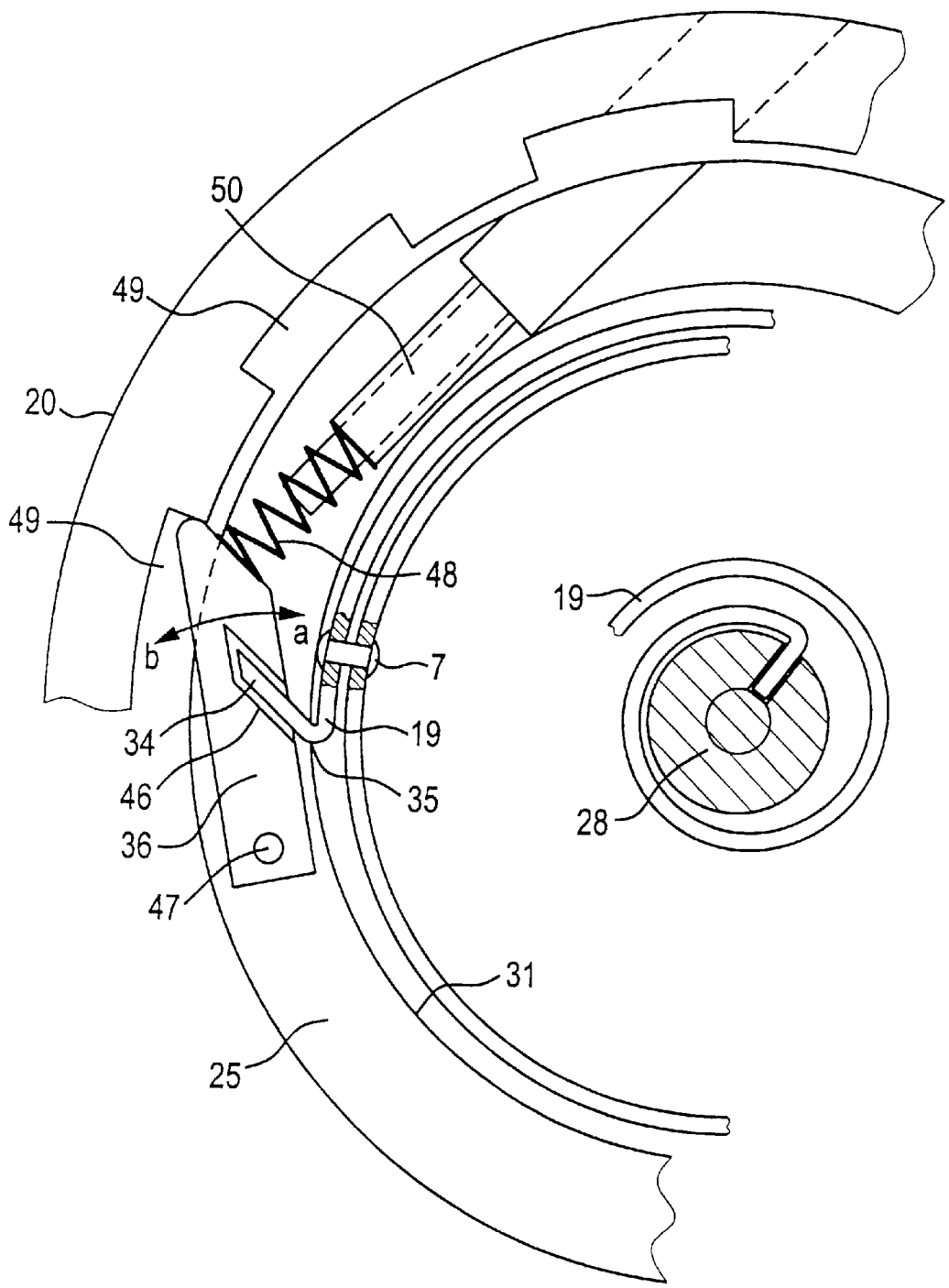
FIG. 3 is a partial cross-section according to the line III—III in FIG. 2 of another inventive weight compensating apparatus.

A variation of the invention is shown in FIG. 3. As partly described above, in this variation the other end 34 of the spring 19 is angled somewhat radially in relation to the cable drum 17 and engages in a slot 46 of the catch 36 of another stopping arrangement. The catch 36 is mounted in swivelling fashion at the cylindrical portion 25 of the cable drum 17, for example, at an axle 47 oriented parallel to shaft 28. A catch spring 48 engages the region of the end of the catch 36 opposite the axle 47, the catch 36 being pushed by the catch spring 48 somewhat radially outwardly in the direction of the housing 20 given the non-stressed condition of the spring 19 direction (b). At the inner shell surface of the housing 20, recesses 49 are fashioned in which the catch 36 engages given the non-stressed condition of the spring 19. The catch 36 is arranged therein such that it prevents a displacement of the cable drum 17 due to the weight acting on the supporting cable 15. As previously explained, when the spring 19 is biased, a force emanating from the spring 19 acts on the catch 36. If the force applied by the spring 19 due to excessive biasing thereof exceeds the force produced by the catch spring 48 which opposes a displacement of the catch 36, then the catch 36 gradually displaces from the recess 49 in the direction of the shaft 28 direction (a), until the blocking is finally cancelled (released). The force of the catch spring 48 acting on the catch 36 is inventively proportioned such that a corresponding displacement of the catch 36 results in the blocking being cancelled only when at least 50% of the counterforce produced by the spring 19 is attained relative to the weight acting on the supporting cable 15, preferably only when 75% is attained. To increase the sensitivity given a spring breakage, the catch spring 48 and the spring 19 can be dimensioned to cancel blocking only when 90% of this weight is attained. It is an advantage of this inventive embodiment that, given a reduction of the force of the spring 19 acting on the catch 36—due to a breakage, for example—the catch 36 is thus displaced in the direction of the housing 20, and the cable drum 17 is stopped by the engagement in the recess 49. The danger of injuring an examination subject or of damaging the equipment arranged at the supporting messenger cable 15 due to spring breakage thus no longer exists. In the framework of the invention the force acting on the catch 36—e.g. the catch spring 48—can be adapted to different weights which may be held by the supporting cable 15. In a preferred variation of this embodiment an adjusting mechanism 50, such as a threaded element is provided for this purpose, this being led through the housing 20 to the catch spring 48 and engaging the end thereof facing away from the catch 36. By setting the adjusting mechanism 50 the force of the catch spring 48 acting on the catch 36 thus can be modified so that the sensitivity of the response of the catch 36 is variable.

Figure 4:
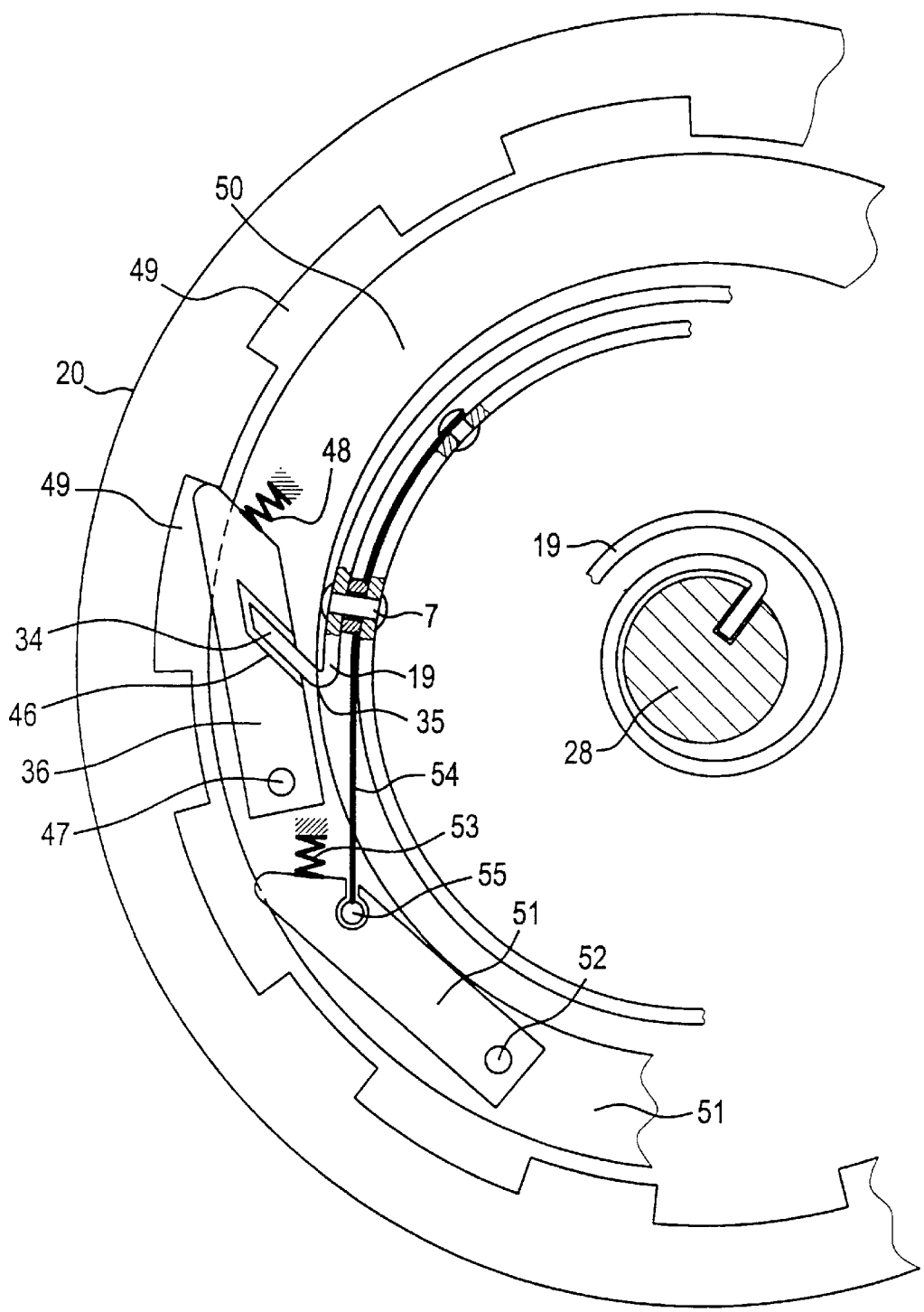
FIG. 4 is a partial cross-section according to the lines III—III in FIG. 2 of another inventive weight compensating apparatus.

In the exemplary embodiment of another variation of an inventive weight compensating apparatus (FIG. 4), besides the elements already explicated in FIG. 3 another catch 51 of another safety arrangement is provided, this likewise pivoting into one of the recesses 49 by rotation on an axle 52 at the cylindrical portion 25 of the cable drum 17, by the force of a further catch spring 53. This further safety arrangement includes a cable 54, one end 55 of which engages the catch 51. The cable 54 extends at least along the outer region of the spring 19, at which it is secured with its other end at a rivet by means of a loop, for example. The length of the cable 54 is dimensioned such that it exerts a tractive (pulling) force on the catch 51, so that this tractive force releases the cable drum 17 in opposition to the force of the catch spring 53. The tensile strength of the cable 54 is dimensioned such that the cable 54 breaks if and when the spring 19 breaks. The catch 51 is then displaced into the recess 49 by the force of the catch spring 53, which cause a stoppage of rotation of the cable drum 17. As noted above a breakage of the spring 19 in the outer region can also cause a stoppage of the cable drum 17. In the framework of the invention a number of cables such as cable 54 can respectively engage other catches such as catch 51. The cable 54 can alternatively be implemented as ribbon, however. Two safety elements effecting a blocking of the displaceability of the cable drum 17 given a breakage of the spring 19 are consequently provided in this variation of the invention.

Figure 5:
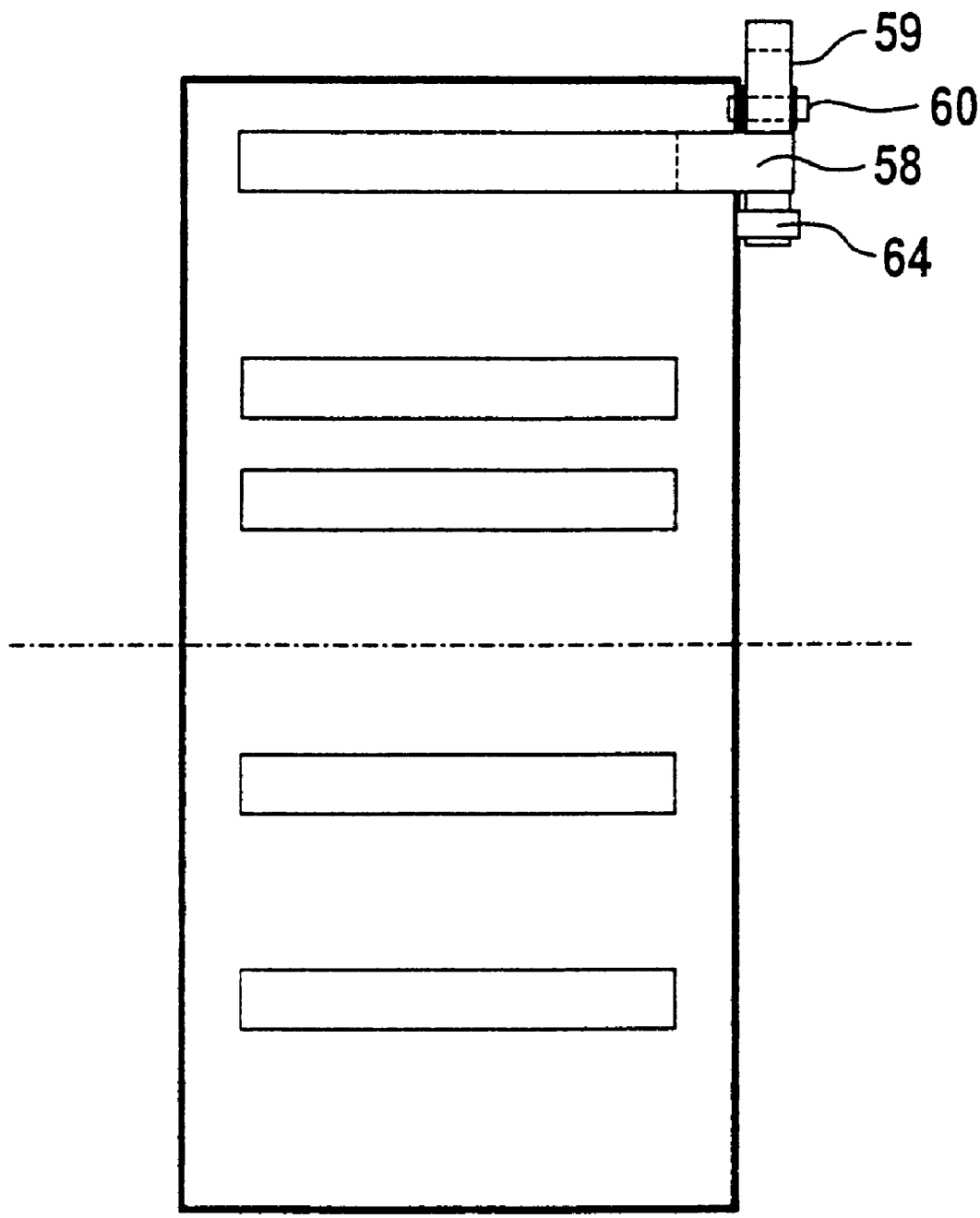
FIG. 5 is a longitudinal section through another inventive weight compensating apparatus.
Figure 6:
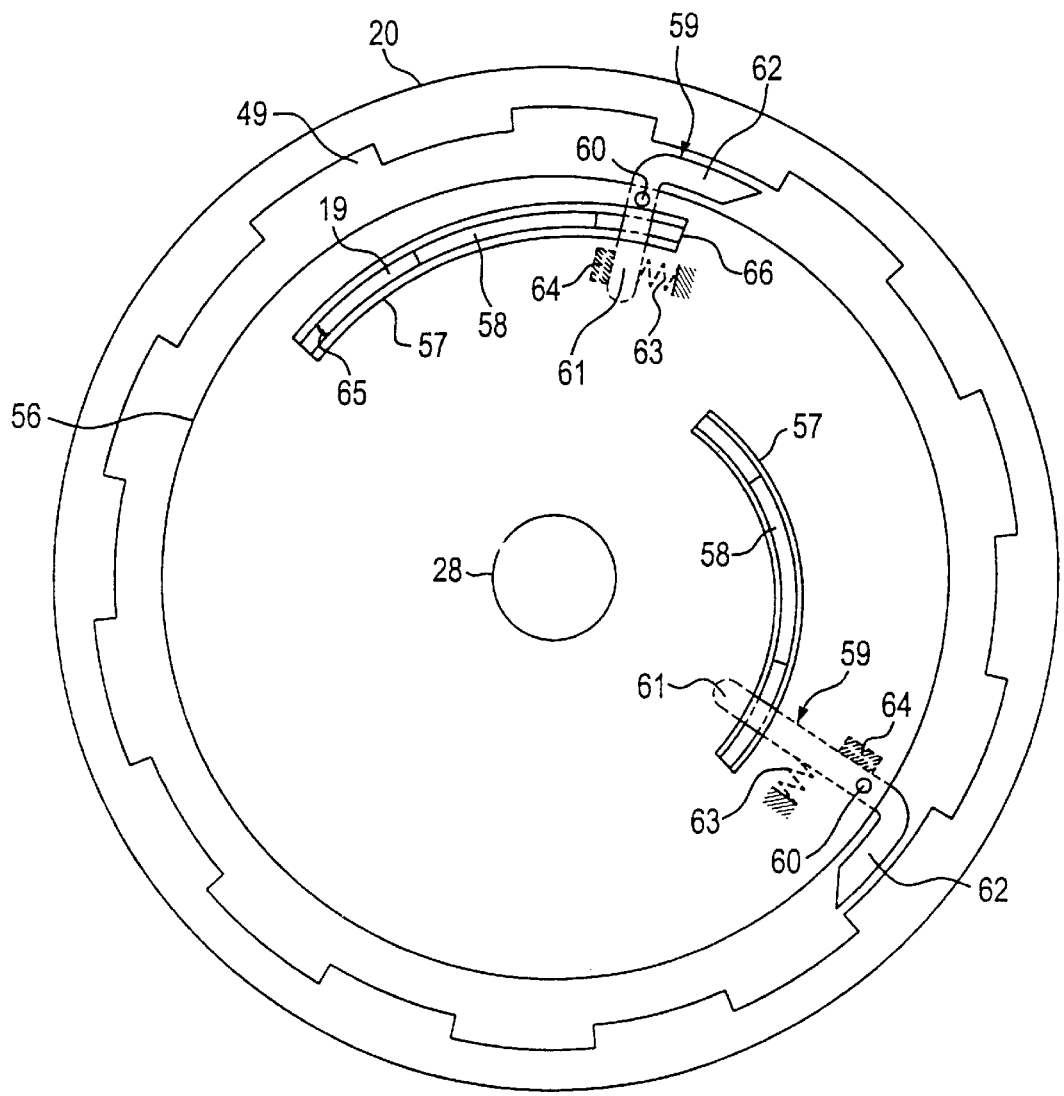
FIG. 6 is a plan view of the spring housing of the exemplary embodiment of the inventive weight compensating apparatus according to FIG. 5.

Another exemplary embodiment of a weight compensating apparatus is described below with reference to FIGS. 5 and 6. This embodiment includes a second spring housing 56 with an extended recess 57 from which a tab 58 of the spring 19 projects over the lateral limiting wall of the second spring housing 56 so far that this tab 58 is suitable for engaging a third catch 59 of a locking mechanism. The catch 59 is arranged at the second spring housing 56 (FIG. 6). The third catch 59 can be rotated around a third axle 60 arranged at the second spring housing 56 in offset fashion parallel to the shaft 28 (FIGS. 5 and 6). The third catch 59 has two legs 61, 62 which assume an angle of about 90° to one another, for example. The first leg 61 projects in one direction toward the shaft 28 and beyond the extended recess 57 and, loaded by the force of a leg spring 63, is forced against a blocking bolt 64 which is likewise mounted at the second spring housing 56 and arranged parallel to the shaft 28 in offset fashion. The second leg 62 is fashioned for engagement in at least one recess 49 of the locking mechanism of the housing 20 (FIG. 3). If the spring 19 breaks at a point such as the breaking point referenced 65, then the tab 58 is displaced in its extended recess 57—due to spring force—in a clockwise fashion to the right end 66 in FIG. 6, thereby engaging the first leg 61 such that this is pivoted around the third axle 60. The second leg 62 is thereby also displaced in the radial direction toward the housing 20, so that it can engage in a recess 49. As already explained, a displacement of the cable drum 17 is prevented by the engagement in the recess 49. In the framework of the invention other extended recesses 57 for other tabs 58 of the spring 19 can be provided, as well as other third catches 59 (FIG. 6). In the framework of the invention the tab 58 can be fashioned as an integral part of the spring 19, but it can also engage the spring 19 as a separate part, which then has to be mechanically connected thereto in suitable fashion.

Figure 7:
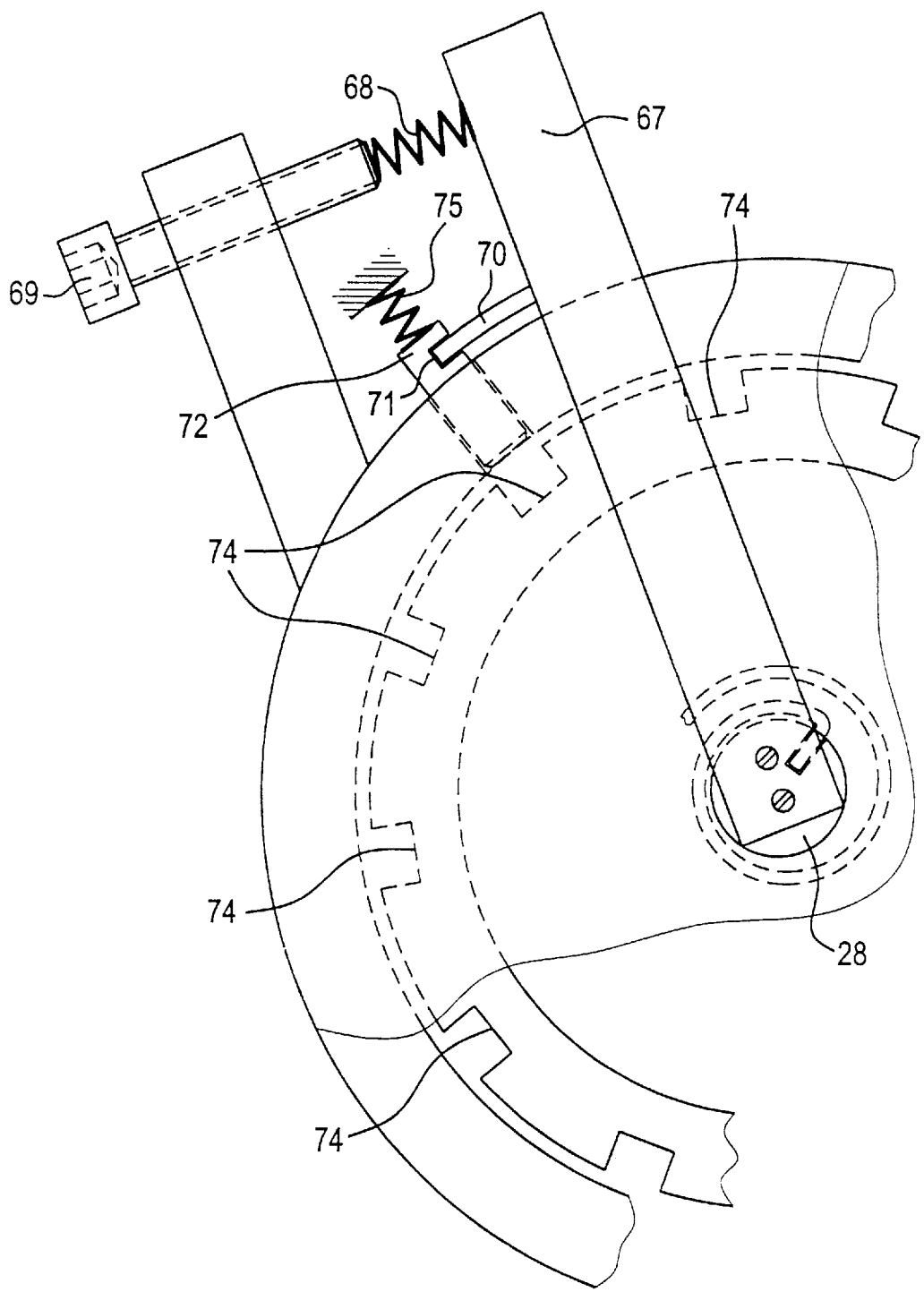
FIG. 7 is a partial cross-section through a further embodiment of the inventive weight compensating apparatus.

A lever 67 is coupled at the shaft 28, this lever 67 extending in the radial direction of the housing 20 (FIG. 7). A lever spring 68 engages the lever 67, the spring force thereof being adjustable via a threaded element 69 acting thereon, for example. The force of the lever spring 68 acting on the lever 67 is proportioned such that the force produced by the spring 19 and acting on the lever 67 in the stressed (biased) condition of the spring 19 is cancelled. A lever nose 70 fashioned for engaging in a bolt recess 71 of a bolt 72 is disposed at the lever 67. Given stressing of the spring 19 the bolt 72 should be held in a position wherein the lever nose 70 reaches into the bolt recess 71 due to the displacement of the lever 67—counter-clockwise according to FIG. 7. The bolt 72 projects through an opening 73 in the housing 20, so that it does not engage in spring housing recesses 74. If the spring 19 breaks, the force acting on the lever 67 diminishes, whereby the lever nose 70 is displaced (in the clockwise direction) from the bolt recess 71. The bolt 72 is then displaced into the spring housing recess 74 by the bolt spring 75 acting at the bolt 72, thus effecting a stoppage of the cable drum 17.

Figure 8:
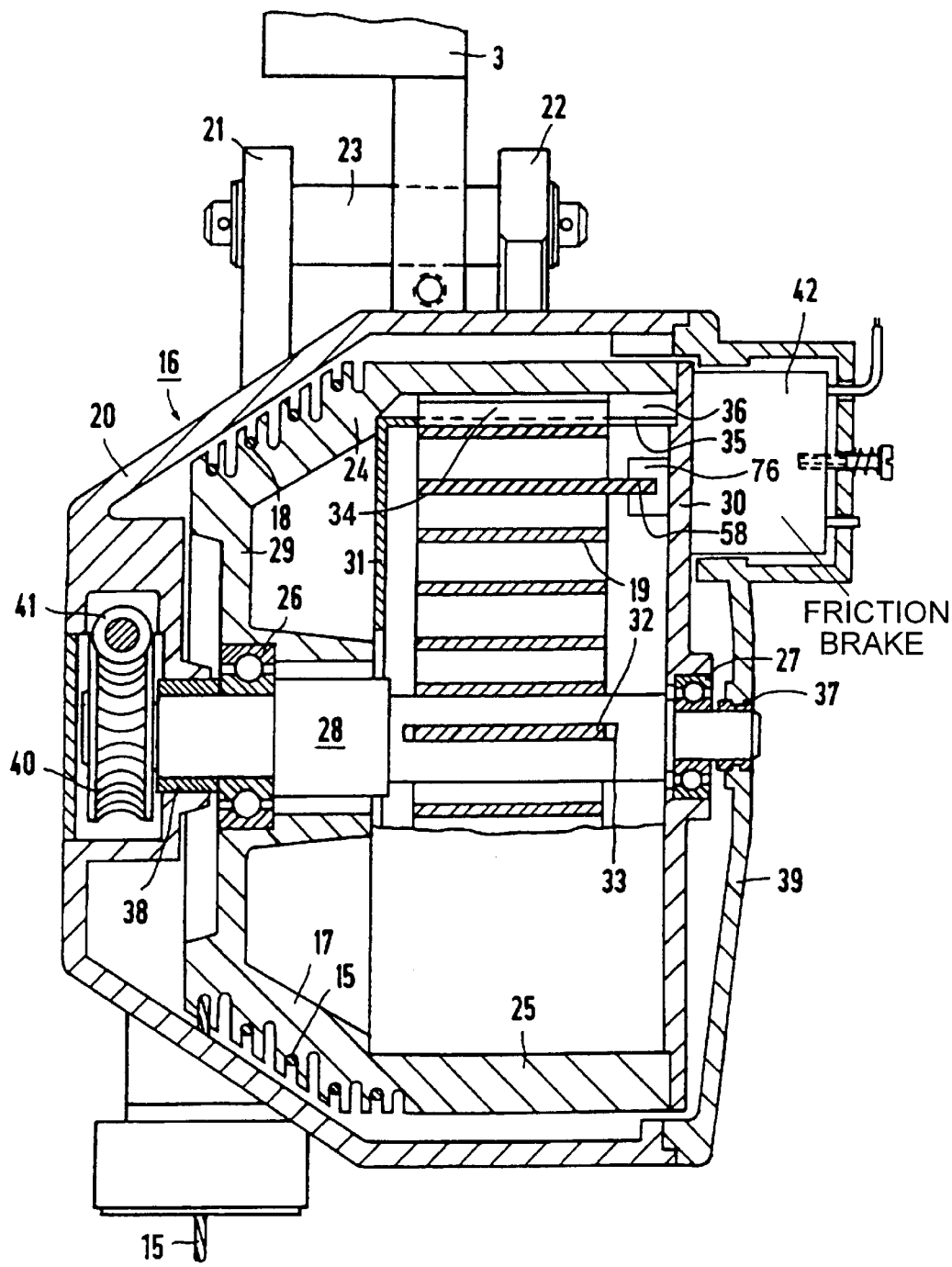
FIG. 8 is a longitudinal section through another embodiment of the inventive weight compensating apparatus.
Figure 9:
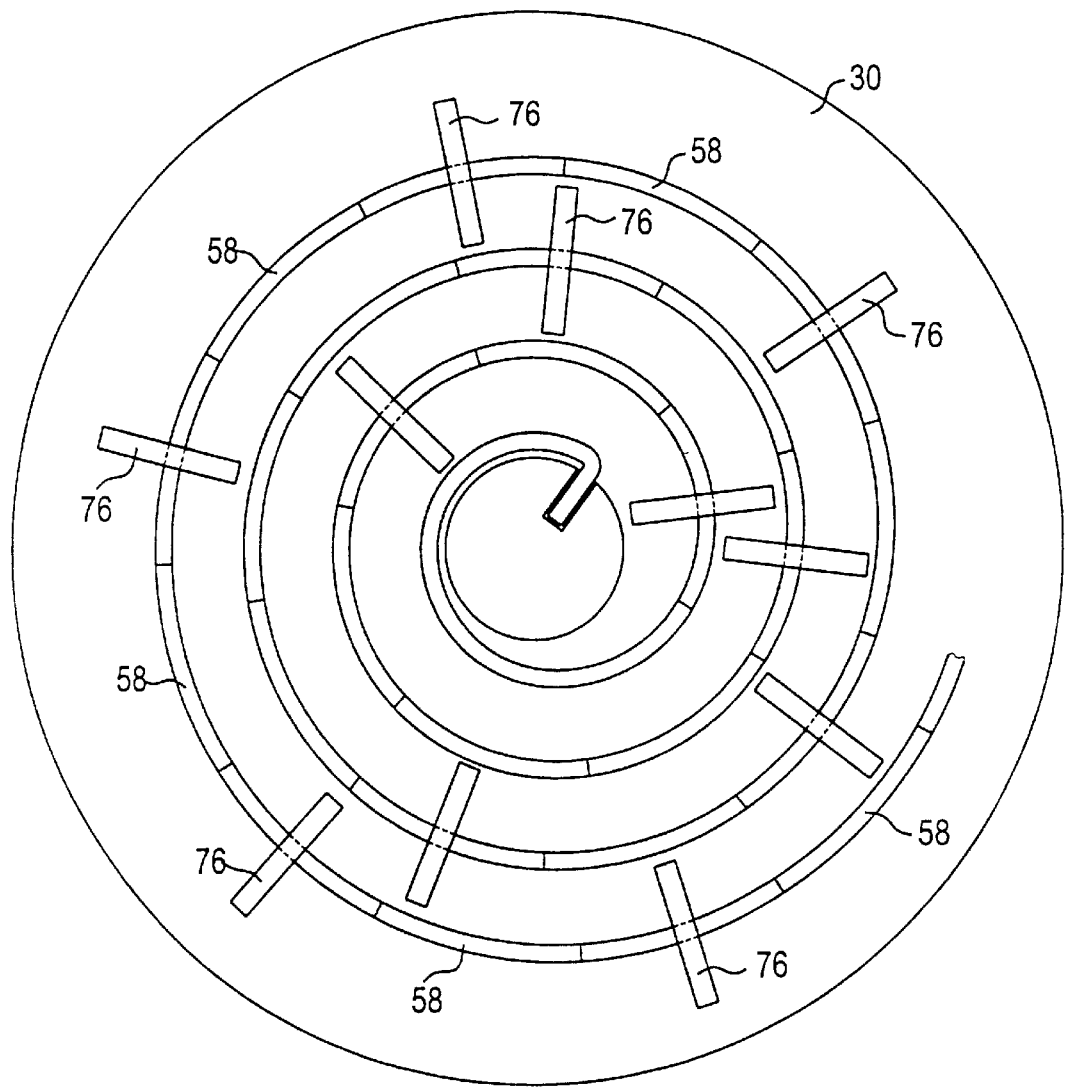
FIG. 9 is a cross-section through the weight compensating apparatus according to FIG. 8.

In the exemplary embodiment of an inventive weight compensating apparatus depicted in FIG. 8, bearing shield noses 76 are fashioned at the inner wall of the bearing shield 30 oriented toward the spring 19. Tabs 58 of the spring 19 are respectively disposed between the noses 76 similarly to the exemplary embodiment according to FIGS. 5 and 6, as can be seen in FIG. 9. If the spring 19 breaks then the tab 58 following the breakage point—and thus the spring 19—are caught at the correspondingly allocated bearing shield nose 76. The compensating force acting on the supporting messenger 15 from the spring 19 thereby diminishes, and a displacement of the x-ray radiator 1 arranged at the telescoping column 2 ensues. However, the counterforce to be applied by the operator to hold the x-ray radiator 1 is much lower, depending on the point of breakage, since a significant counterforce still acts from the spring 19 on the bearing shield nose 76—and thus on the cable drum 17—via the tab 58. Without such a development the entire counterforce emanating from the spring 19 would be virtually entirely cancelled given a breakage of the spring 19.

In a further exemplary embodiment of the invention that is not shown in the drawings, the spring 19 is arranged for reasons of safety in a tin housing from which a torque acts on the cable drum 17 given a stressed spring 19. A catch is held by this torque in a position which releases the cable drum 17 for adjustment. If the torque is reduced due to a spring breakage, the catch is displaced such that it blocks the cable drum 17 from a further displacement.

Figure 10:
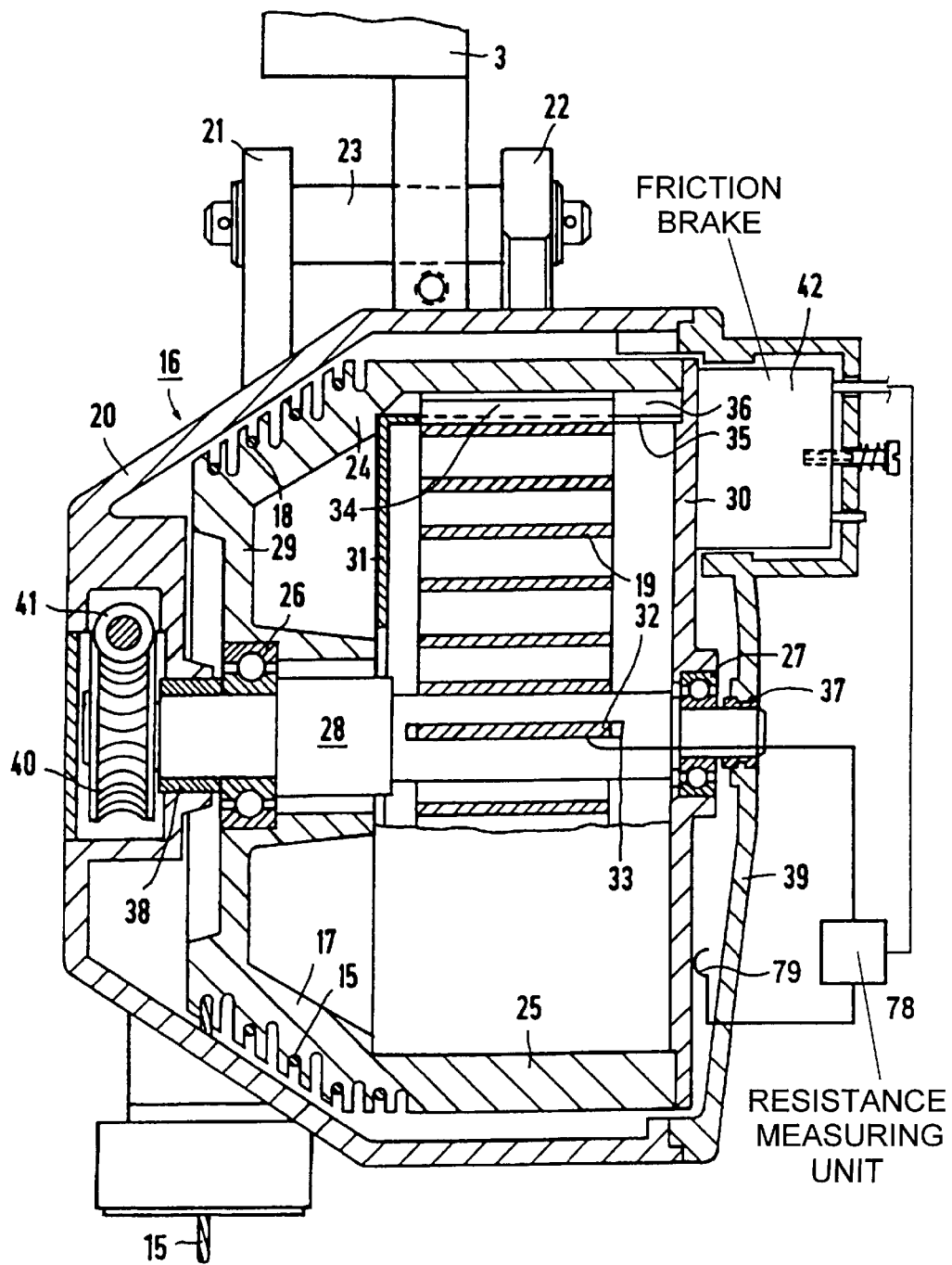
FIGS. 10–13 respectively show exemplary embodiments for the electrical detection of a spring breakage in an inventive weight compensating apparatus.
Figure 11:
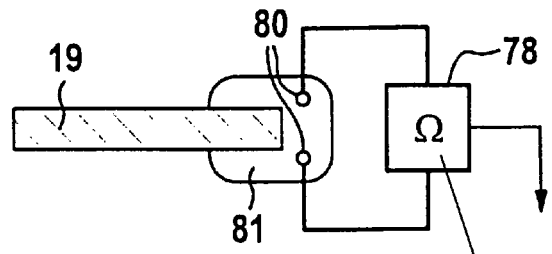

An arrangement for detecting a spring breakage of a weight compensating apparatus wherein the resistance of the spring 19 is measured is shown in FIG. 10, for example. The individual turns of the spring 19 are insulated from each other to this end, which can be accomplished by an intervening of an insulating material. The inner end 77 of the spring 19 engaging the shaft 28 is held at the shaft 28 in insulated fashion. A first terminal of a resistance measuring unit 78 is connected to this inner end 77. The outer end of the spring 19 is not insulated, so that an electrical contact to the bearing shield 30 is guaranteed. A second terminal of the resistance measuring unit 78 is connected to the bearing shield 30, for example, via a loop contact 79, for example, so that the resistance of the spring 19 can be measured via the resistance measuring unit 78. If the resistance of the spring 19 changes due to a breakage, for example, the resistance measuring unit 78 generates a control signal which is fed to the friction brake 42—as example of an electromechanically controllable stopping means—for the actuation thereof. It is thus guaranteed that a displacement of the cable drum 17 does not ensue given a breakage of the spring 19. In the framework of the invention a resistance wire 80 can extend in a loop at least along a subregion of the spring 19, this being arranged at the spring 19 via a U-shaped insulating body 81, for example (FIG. 11). The resistance of the resistance wire 80 can also be detected therein via the resistance measuring unit 78 connected to the resistance wire 80. Given a breakage of the spring 19 the resistance wire 80 also breaks, so that a signal for actuating the friction brake 42 with respect to the stopping of the cable drum 17 is generated via the resistance measuring unit 78.

Figure 12:
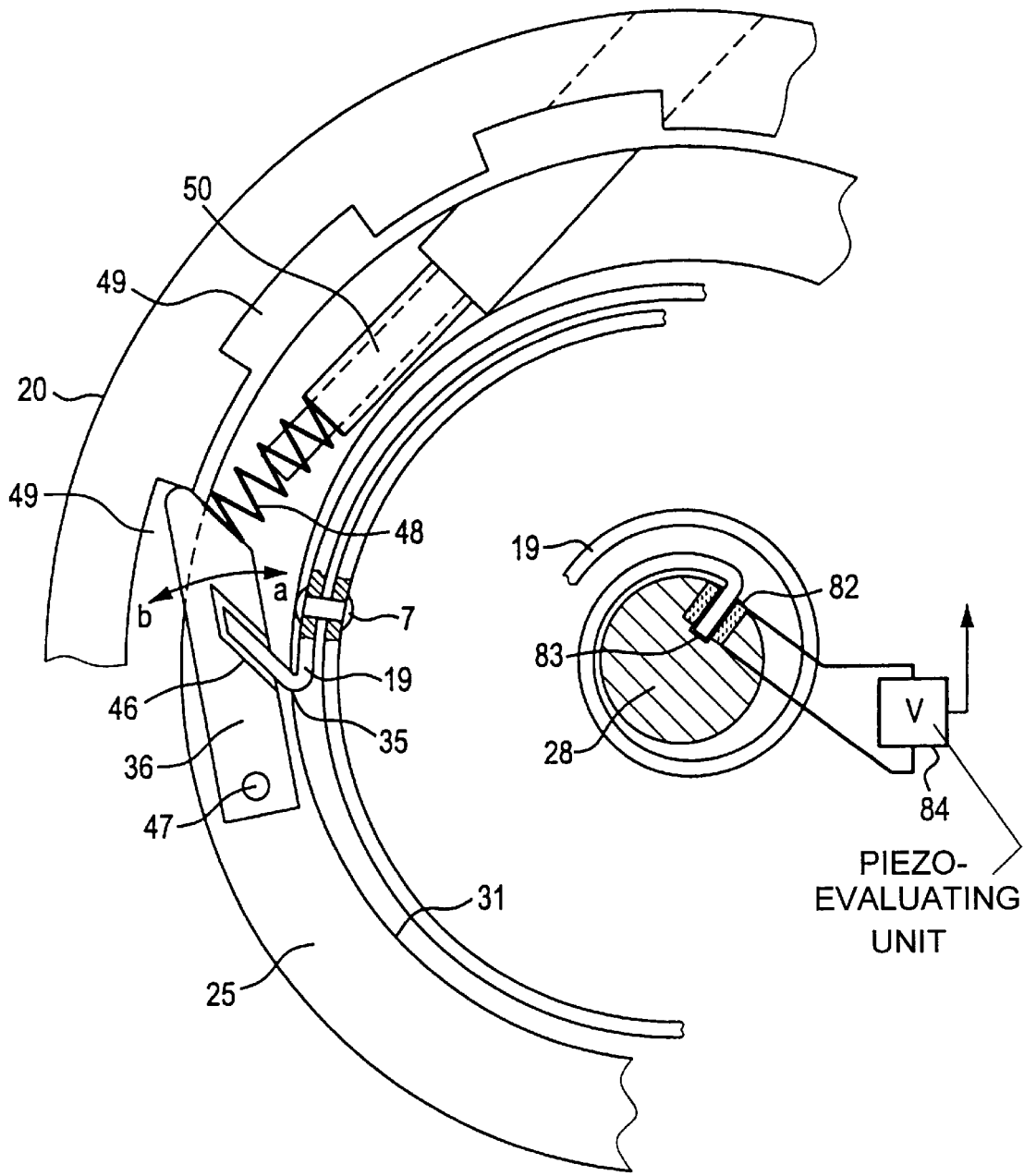

In the exemplary embodiment depicted in FIG. 12 the spring force of the spring 19 is detected and, given an impermissible or insufficient counterforce, a signal for the actuation of the friction brake 42 for the stopping the cable drum 17 is generated. In the exemplary embodiment a piezo-element 82 is arranged between the end 32 of the spring 19 and a shaft slot 83 of the shaft 28. The pressure-dependent signal of the piezo-element 82 is detected via a piezo-evaluating unit 84 and, as previously explained, a signal for the actuation of the friction brake 42 is generated if an insufficient force is acting on the shaft 28. The piezo-element 82 could likewise be arranged in the region of the outer end of the spring 19, however. According to this embodiment of the invention it is essential to detect the force of the spring 19 by means of a piezo-element 82, a pressure measuring device, or extension element and to generate a control signal if the force emanating from the spring 19 is too slight.

Figure 13:
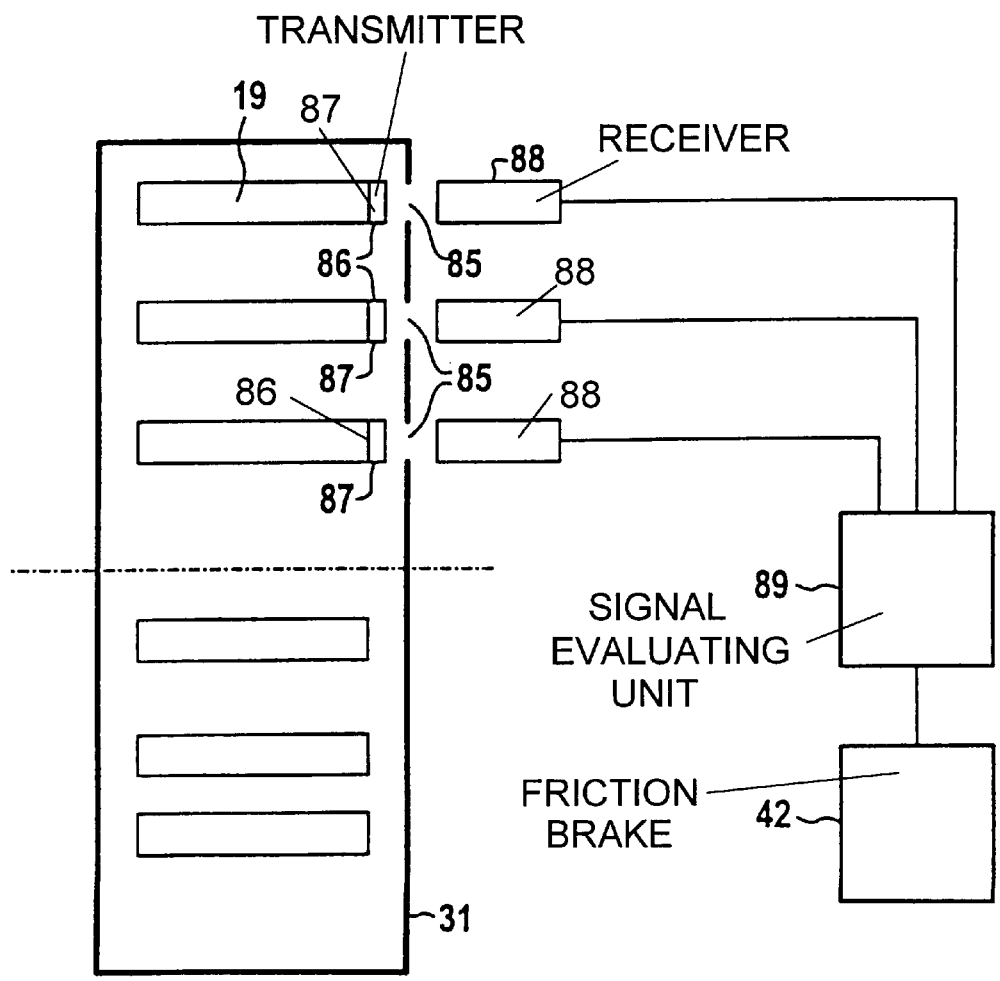

In the exemplary embodiment of an arrangement for detecting a spring breakage depicted in FIG. 13 recesses 85 are provided in the spring housing 31. According to one variation, transponders can be provided at the lateral face 86 of the spring 19; according to another variation, magnets or other kinds of transmitters 87 can be provided. Signals are generated via a receiver 88—which transmits a signal to the transponder and queries its position in the first exemplary embodiment, and which is implemented as magnetic coil in the second exemplary embodiment—these signals being subsequently fed to a signal evaluating unit 89. A signal dependent on spring breakage can thus be detected by the signal evaluating unit 89, which subsequently supplies a control signal to the friction brake 42 for stopping the spring drum 17.

In the framework of the invention general stopping means for direct or indirect stopping of the cable drum 17 can also be used.

Furthermore, the use of an inventive weight compensating apparatus is not restricted to medical technology only. Such weight compensating apparatuses can be employed anywhere where tools or other means are held in balanced fashion with respect to weight.

Although the present invention has been described with reference to a'specific embodiment, those of skill in the art will recognize that changes may be made thereto without departing from the scope and spirit of the invention as set forth in the appended claims.

I claim as my invention:

1. A weight compensating apparatus comprising:

a load;

a supporting cable supporting said load;

a rotatable cable drum on which said supporting cable is wound for winding and unwinding said supporting cable from said cable drum dependent on a direction of rotation of said cable drum;

a spiral spring element mechanically engaging said cable drum and exerting a force on said cable drum to bias said cable drum counter to a force produced by a weight of said load;

arresting means engageable with said cable drum for stopping rotation of said cable drum; and safety means for triggering said arresting means for stopping said rotation of said cable drum upon a breakage of said spiral spring element, including a breakage at an outer region of said spiral spring element, said safety means comprising a catch biased by a catch spring and engaging an outer end of said spiral spring element, said catch normally precluding said arresting means from stopping rotation of said cable drum, said catch spring being dimensioned to produce a catch spring force, relative to said force produced by said spiral spring element, to preclude said arresting means from stopping rotation of said cable drum only as long as said spiral spring element produces a force corresponding to at least 50% of said weight of said load.

2. A weight compensating apparatus as claimed in claim 1 wherein said catch spring produces a catch spring force which precludes said arresting means from stopping rotation of said cable drum only as long as said spiral spring element produces a force corresponding to at least 90% of said weight of said load.

3. A weight compensating apparatus as claimed in claim 1 further comprising means for adjusting said catch spring force of said catch spring.

* * * * *